United States Patent [19]

Hon

[11] Patent Number: 4,541,439

[45] Date of Patent: Sep. 17, 1985

[54] MONITORING OF CAPILLARY BLOOD FLOW

[75] Inventor: Edward H. Hon, Bradbury, Calif.

[73] Assignee: American Home Products Corporation (Del.), New York, N.Y.

[21] Appl. No.: 371,370

[22] Filed: Apr. 23, 1982

[51] Int. Cl.[4] .............................................. A61B 5/02
[52] U.S. Cl. .................................... 128/691; 128/778
[58] Field of Search ................................ 128/691–692, 128/664, 698, 778, 788; 604/55; 73/196

[56] References Cited

U.S. PATENT DOCUMENTS

| 3,717,031 | 2/1973 | Biscar | 128/692 X |
| 3,739,640 | 6/1973 | Folts | 128/691 X |
| 3,769,974 | 11/1973 | Smart et al. | 128/666 |
| 3,945,250 | 3/1976 | Elazar et al. | 128/691 X |
| 4,300,570 | 11/1981 | Stafl | 128/665 |
| 4,332,258 | 6/1982 | Arai et al. | 128/666 |
| 4,369,773 | 1/1983 | Chvapil | 604/55 X |

FOREIGN PATENT DOCUMENTS 2076963 12/1981 United Kingdom ............... 128/664

OTHER PUBLICATIONS

Goodlin; "Intrapartum Fetal Heart Rate Responses and Plethysmographic Pulse"; *Amer. J. Obstet. Gynec.*; vol. 110, No. 2, 5-1971, pp. 210-226.

Bercovici et al.; "Comparison Between Uterine, Upper Vaginal, Lower Vaginal, and Digital Pulse"; *Amer. J. Obstet. Gynec.*, vol. 98, No. 3, 6-1967, pp. 414-418.

*Primary Examiner*—Lee S. Cohen
*Assistant Examiner*—Angela D. Sykes
*Attorney, Agent, or Firm*—Edward M. Blocker

[57] ABSTRACT

The monitoring of capillary blood flow in a woman's cervical wall and vaginal wall is provided so that the capillary blood flow patterns therein may be compared in order to evaluate various physiological conditions of the woman. In addition, methods are provided for comparing one or both of such capillary blood flow patterns with patterns of capillary blood flow obtained from the woman's forehead at the anastomoses of the supratrochlear branches of the ophthalmic artery, for evaluating a physiological condition of a woman. Systems and devices for carrying out these evaluations, as well as for observing such capillary blood flow patterns separately, are provided.

27 Claims, 9 Drawing Figures

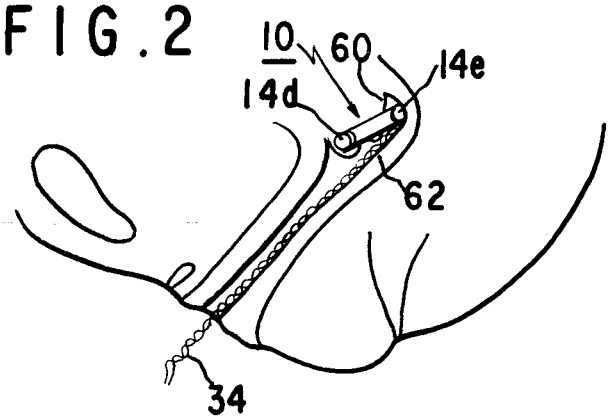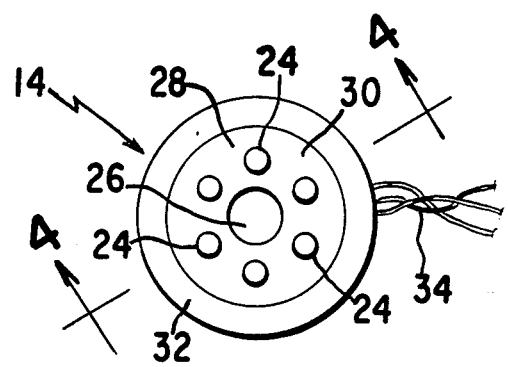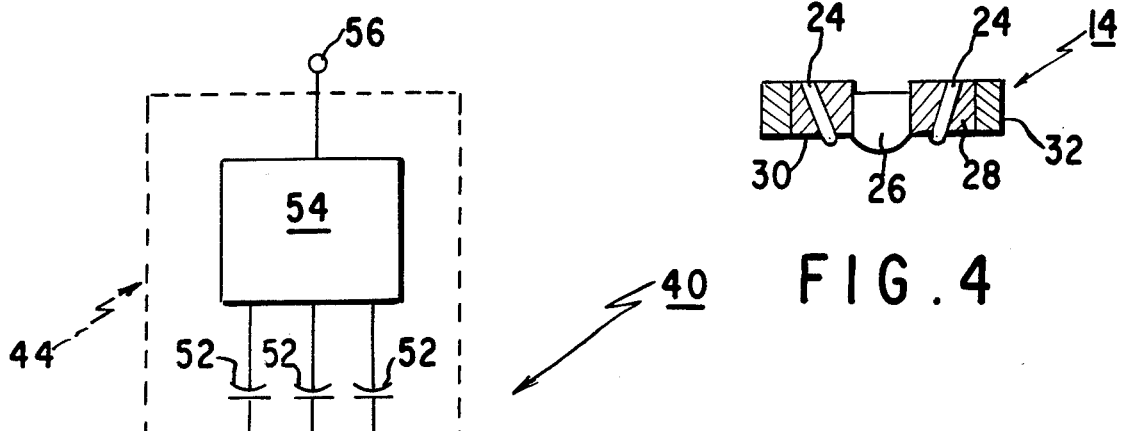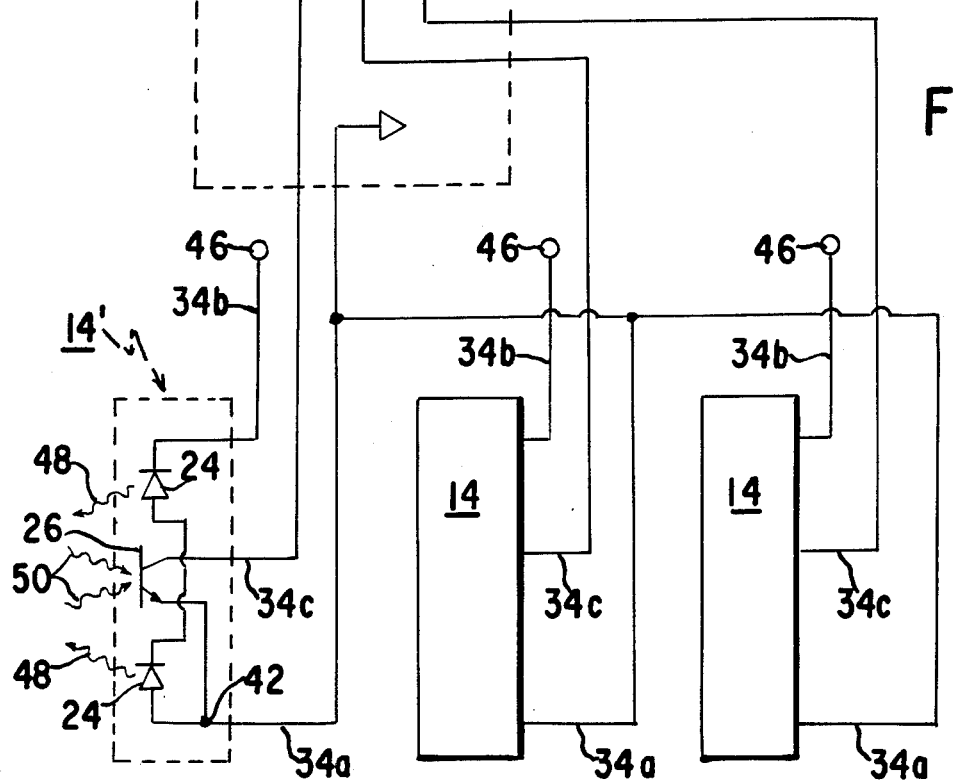

MONITORING OF CAPILLARY BLOOD FLOW

BACKGROUND OF THE INVENTION

The present invention relates to the monitoring of capillary blood flow in a woman's cervix and vagina for the diagnosis of various physiological conditions.

The ability to monitor capillary blood flow in a woman's cervix provides the potential to obtain important physiological data for the diagnosis of a wide range of conditions of concern both in obstetrical and gynecological practice. Even though the status of the pelvic flow has great medical significance, little research has been done in this area. This is primarily due to the absence of adequate, convenient non-invasive instrumentation to collect and reduce capillary blood flow data so that normal and abnormal circumstances can be identified.

During pregnancy, adequate uterine artery blood flow is the most important single factor in fetal growth and development. In situations where it is markedly compromised as the consequence of overt maternal cardiovascular disease, the fetus may be undergrown, or even die. In the human patient, it is not possible to obtain an accurate measurement of uterine blood flow directly with non-invasive techniques. However, the uterine artery supplies not only the corpus of the uterus, but also the cervix uteri and the vagina through its vaginal branches. Hence, it is possible to determine to a large extent, the status of uterine artery blood flow by evaluation of cervical and vaginal capillary blood flow.

The evaluation of uterine artery blood flow is of importance during gestation to determine if it is adequate. It may be compromised by maternal cardiovascular disease, diabetes mellitus, toxemia of pregnancy and other diseases. If the uterine artery flow is diminished, maternal treatment would be reevaluated to find a more efficacious treatment. In circumstances where it is compromised to the point where intact fetal survival is threatened, the gestation would be terminated to save the fetus from irreversible damage or death.

During labor and in the late antepartum period uterine contractions constitute an additional stress to the fetus, since each contraction decreases blood flow to the placenta. Hence, it is doubly important at these times to measure uterine blood flow. Another concern during labor is material hypotension as a consequence of maternal position and/or conduction anesthesia. The presence of hypotension adds an additional fetal hazard.

The woman's uterus and vagina are both supplied with blood by the uterine artery. Capillary blood flow in the cervix and vagina is related directly to uterine artery flow. The ability to monitor continuously such capillary flow provides the potential for acquiring data of clinical significance e.g., uteroplacental insufficiency, the effect of uterine contraction on uterine blood flow.

Maternal hypotension can result from blockage of the veins returning blood to the heart from the pelvis as a result of pressure exerted by the uterus. This is apt to occur especially in the case of the patient with conduction anesthesia, inasmuch as her blood tends to pool in the pelvis. The reduced input of blood to the heart as a consequence of these conditions leads to reduced cardiac output and consequent hypotension. This condition is potentially dangerous to the fetus due to the consequent reduction in the flow of oxygenated blood to the uterus.

SUMMARY

Circulatory conditions specific to the uterus must be distinguished clinically from those affecting pelvis blood flow more generally. Therefore, to accurately diagnose the condition of the mother and the fetus in the intrapartum, and in the late antepartum, it is necessary both to obtain an indication of uterine blood flow, as well as a more general indication of pelvic blood flow. Such a capability is provided by the simultaneous monitoring of cervical capillary blood flow and vaginal capillary blood flow.

It is also desirable to obtain a comparison of pelvic blood flow with a more general indicator of the condition of the mother's circulatory system. Such an indication is provided by monitoring capillary blood flow in the woman's forehead where the supratrochlear branches of the ophthalmic artery anastomose. A comparison of pelvic blood flow with the general pattern of flow in the maternal circulatory system provides additional significant information for conditions such as maternal hypertension.

The ability to monitor cervical capillary blood flow simultaneously with the monitoring of a more general condition of blood flow in a woman's circulatory system also provides the potential for detecting the time of ovulation inasmuch as the cervix typically at that time becomes somewhat more vascular. This same comparison also provides the potential for seeking the cause of dysmenorrhea, which may result either from uterine contractions or from a diverse cause which is neither vascular nor contractile, such as a uterine tumor.

In accordance with one aspect of the present invention, therefore, a method is provided of evaluating the physiological condition of a woman, comprising the steps of: producing a first signal representative of capillary blood flow in the woman's cervix; producing a second signal representative of capillary blood flow in the woman's vagina; and comparing the first and second signals.

In accordance with a further aspect of the present invention, a method is provided of evaluating the physiological condition of a woman comprising the steps of: producing a first signal representative of capillary blood flow in the woman's cervix or vagina; producing a second signal representative of capillary blood flow in the woman's forehead at the anastomosis of the supratrochlear branches of the ophthalmic artery; and comparing the first and second signals.

It is a further object to provide devices adapted for producing such capillary blood flow signals from the cervical and vaginal walls.

It is a still further object of the present invention to provide such devices capable of fitting variously sized cervices.

It is yet another object to maintain the capillary blood flow sensors of the device in stable contact with the vaginal and uterine walls despite the patient's movements.

A further object is to provide such devices which will avoid undue irritation of vaginal and cervical tissues.

In accordance with still another aspect of the present invention, a device is provided for use in monitoring cervical and/or vaginal capillary blood flow. The device comprises a support adapted to be held between the vaginal wall and the cervical wall of a woman, and means for sensing capillary blood flow. The sensing means is positioned on the support to contact one of the cervical wall and the vaginal wall for sensing capillary blood flow therein.

In accordance with an advantageous embodiment of the present invention, this support is adapted to be expanded when placed between the cervical wall and the vaginal wall such that it presses against and is held by at least one of the vaginal and cervical walls. It is thus possible to provide a device which is sized for ease of placement between the vaginal and cervical walls, but which thereafter expands to fit snuggly therebetween.

In accordance with a further advantageous embodiment of the present invention, the support is capable of being modified at the time of clinical use to conform to a woman's cervix. Accordingly, the embodiment being adaptable to various cervices, it is not necessary to manufacture a large variety of devices to accommodate these variations.

BRIEF DESCRIPTION OF DRAWINGS

The present invention, as well as further objects and features thereof, will be understood more clearly and fully from the following description of certain preferred embodiments, when read with reference to the drawings, in which:

FIG. 2 is a sectional view of a woman's vagina and cervix, with the device of FIG. 1 or of FIG. 1A in place therein for monitoring cervical and vaginal capillary blood flow;

FIG. 3 is a bottom plan view of a capillary blood flow sensor for use in the embodiment of FIGS. 1 and 1A;

FIG. 4 is a sectional view of the sensor of FIG. 3 taken along the lines 4—4 in FIG. 3.

FIG. 5 is a schematic diagram of a system for monitoring cervical and/or vaginal capillary blood flow, in accordance with the present invention;

DETAILED DESCRIPTION OF CERTAIN PREFERRED EMBODIMENTS

Figure 1:
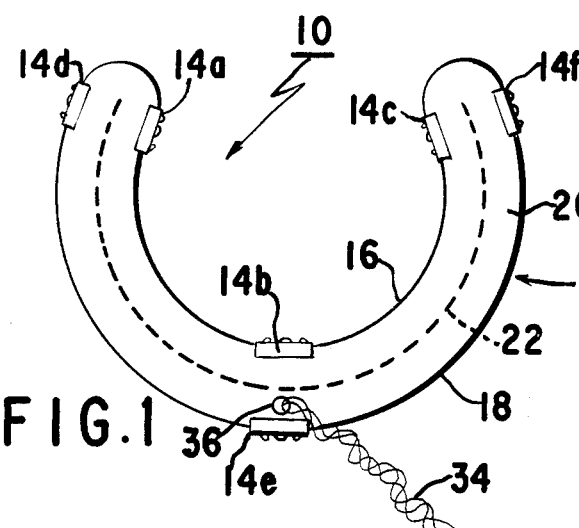
FIG. 1 illustrates a device for use in monitoring cervical and/or vaginal capillary blood flow, in accordance with one aspect of the present invention.

With reference first to FIG. 1, a device 10 for use in monitoring cervical and/or vaginal capillary blood flow is illustrated. The device 10 includes a support 12 adapted to be held between the vaginal wall and the cervical wall of a woman. The support 12 has a toroidal shape and is dimensioned accordingly for placement between the vaginal and cervical walls. The toroidal support 12 extends at least about two thirds of a circle.

Three capillary blood flow sensors 14a, 14b and 14c are located on an inner, concave surface 16 of the support 12 at intervals of about one third of a circle for contacting the cervical wall to sense capillary blood flow therein. Three additional capillary blood flow sensors 14d, 14e and 14f are positioned on an outer, convex wall 18 of the support 12 at angular intervals of about one third of a circle for contacting the vaginal wall to sense capillary blood flow therein. Sensors 14a–f are described in greater detail below in connection with FIGS. 3 and 4.

The support 12 includes a cushion 20 made of a sponge material which is non-reactive and may be, for example, silicone, dacron or nylon. The cushion 20, therefore, is adapted to absorb fluids and consequently expands as the fluids are accumulated. Accordingly, when the device 10 is placed between the cervical wall and the vaginal wall, vaginal fluids are absorbed by the cushion 20 causing it to expand and press against the vaginal and cervical walls, such that it is held snuggly therebetween. At the same time, the sponge cushion 20 presses softly against the tissues in order to avoid undue irritation thereof.

The support 12 also includes a form-sustaining spine 22 embodied in the cushion 20 such that it does not come in contact with the bodily tissue. Spine 22 is made of a bendable material, so that at the time of clinical use, the device 10 may be expanded radially or contracted radially to accommodate the size of a particular patient's cervix.

Figure 1A:
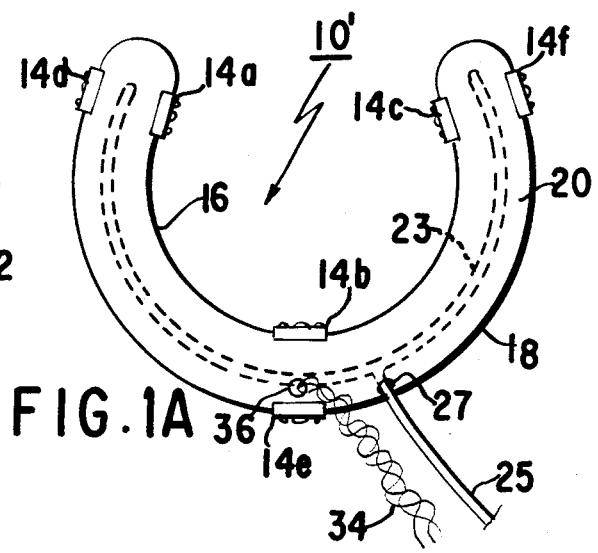
FIG. 1A illustrates a further device for use in monitoring cervical and/or vaginal capillary blood flow, in accordance with another aspect of the present invention.

With reference now to FIG. 1A, wherein elements corresponding to those of FIG. 1 are designated by the same reference numerals, a modified device 10' is illustrated for use in monitoring cervical and/or vaginal capillary blood flow. The device 10' includes an expandable bladder 23 disposed within cushion 20 and adapted to be expanded when inflated with fluid, such as saline solution. A filling tube 25 communicates with bladder 23 at a first end of tube 25 and extends therefrom outwardly of cushion 20 through an aperture 27 therein. Tube 25 provides a means for inflating the bladder 23 within cushion 20 so that the cushion may be expanded to fit snugly between the cervical wall and the vaginal wall.

FIG. 2 illustrates a manner in which the devices of FIGS. 1, and 1A may be positioned between the cervical wall 60 and the vaginal wall 62 of a woman. Device 10 or 10' is introduced through the vagina and pressed upwardly between the cervical wall 60 and vaginal wall 62 along the posterior and lateral sides thereof. Accordingly, the sensors 14a–c on the inner concave surface of the devices 10' and 10 face toward and are pressed against the cervical wall for monitoring capillary blood flow therein and the sensors 14d–f positioned on the outer, convex wall of the devices 10 and 10' face toward and are pressed against the vaginal wall 62 to sense capillary blood flow therein. The wires 34 lead through the vagina and outwardly thereof for coupling to monitoring circuitry, such as that described below in connection with FIG. 5. In the case of the device 10' of FIG. 1A, the tube 25 leads through the vagina and outwardly thereof to permit the bladder to be inflated so that the device 10' fits snugly between the cervical wall 60 and the vaginal wall 62.

Figure 1B:
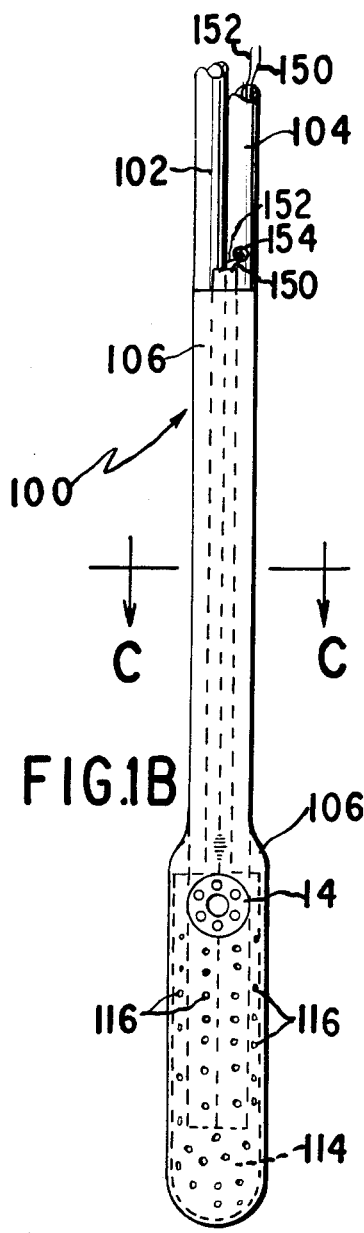
FIG. 1B is a plan view of a device for use, inter alia, in monitoring cervical capillary blood flow.
Figure 1C:
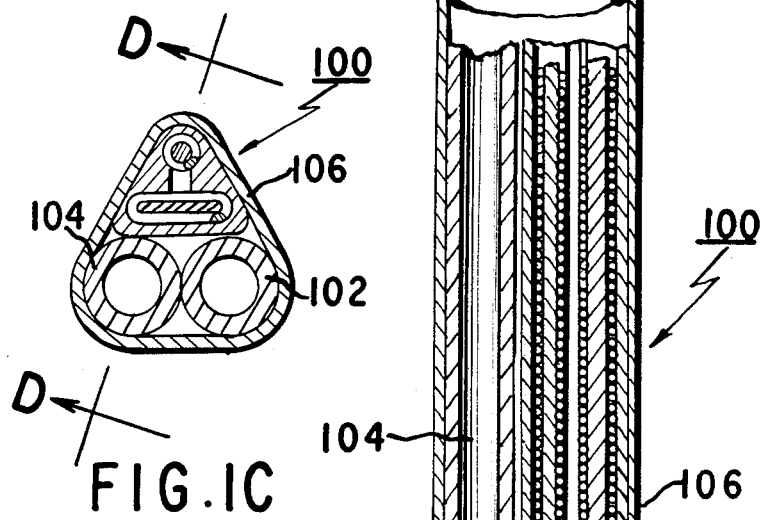
FIG. 1C is a cross sectional view taken along the lines C—C in FIG. 1B.
Figure 1D:
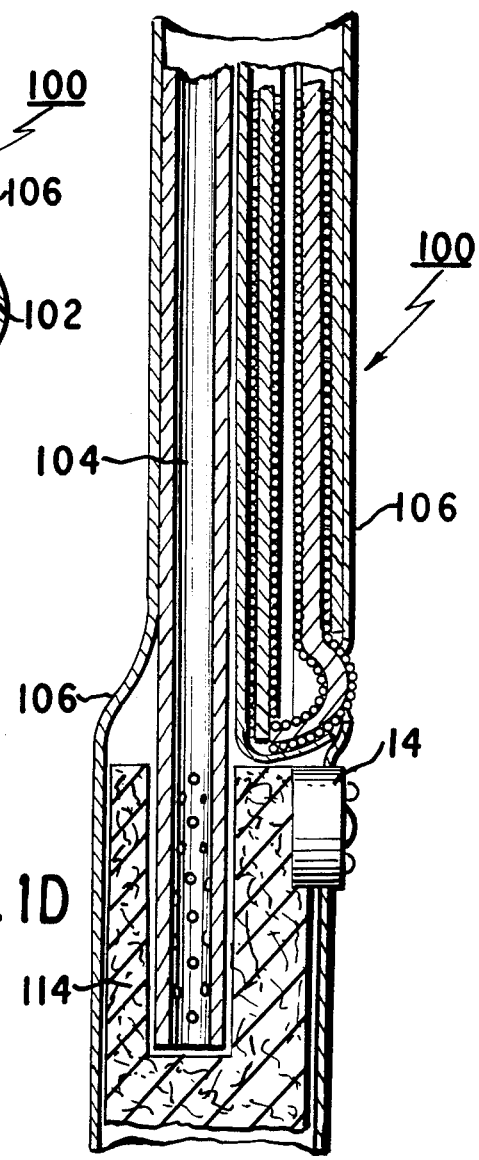
FIG. 1D is a cross sectional view taken along the lines D—D in FIG. 1C.

FIGS. 1B, 1C and 1D illustrate a device 100 for use in monitoring several different physiological parameters during labor, namely, cervical dilatation, intrauterine pressure, material ECG, and cervical capillary blood flow. The ability to monitor cervical capillary blood flow is provided by a sensor 14 corresponding to that described below in connection with FIGS. 3 and 4. The device 100 includes two tubes 102 and 104 in side-by-side relationship and a sponge 114 covering the distal ends of tubes 102 and 104. A cover 106 is disposed over the sponge 114 and a portion of tubes 102 and 104 extending in a proximal direction from sponge 114. Cover 106 has a plurality of pinholes 116 therethrough adjacent its distal end to permit uterine fluids to fill the sponge 114. Sensor 14 is affixed to the sponge 114 adjacent its proximal end and projects outwardly of cover 106. Device 100 is adapted to be positioned between a fetal presenting part and the cervix during labor. Sensor 14 is disposed to face the cervical wall for monitoring capillary blood flow therein. The wires from sensor 14 pass through tube 104 to its proximal end which is disposed outside the vagina for coupling the wires to monitoring apparatus. After the device 100 is in place between the presenting part and the cervical wall, uterine fluids fill the sponge 114 through pinholes 116. As the sponge 114 absorbs uterine fluids, it expands to press the sensor 14 into the cervical wall. At the same time, sponge 114 is yieldable beneath sensor 14 to avoid excessive pressure against the cervical wall. Further details of the device 100 are provided in my U.S. patent application entitled "Monitoring of Cervical Dilatation During Labor" filed concurrently herewith.

With reference now to FIGS. 3 and 4, a sensor 14 representative of each of sensors 14a–f is illustrated. The sensor 14 includes six infrared transmitters 24 arranged about and spaced from a photoresponsive element 26. Each of the infrared transmitters 24 and the photoresponsive element 26 are embedded in a plastic base 28 and protrude through a surface 30 of the base 28. Consequently, when base 28 is positioned to face either the cervical or vaginal wall and as the vaginal fluids are absorbed by cushion 20 in device 10 or 10' each of the associated infrared transmitters and the photoresponsive element are pressed against that cervical or vaginal wall which faces base 28. The protrusion of transmitters 24 and element 26 through the surface 30 aids in minimizing the effects of forces tending to separate each of the sensors from the tissues since both the transmitters and photoresponsive element are pressed into the tissues. Transmitters 24 are angled inwardly of the sensor 14 to transmit infrared radiation to a point in the tissues beneath the element 26. The sensor 14 also includes an annular guard ring 32 defining the lateral border of the base 28. The guard ring 32 is adapted to press against the tissue and block the transmission of any surface waves in the tissue from the surface thereof adjacent the transmitters 24 and the element 26, since such waves may tend to temporarily separate the transmitters 24 and the element 26 from the tissue, introducing artifacts into the signal produced by the sensor 14.

Three wires 34 pass through an aperture (not shown) in the guard ring 32 and pass through the base 28 for connection to the transmitters 24 and the element 26. When the sensors 14a–f are mounted on the devices 10 and 10', their wires 34 are passed through the support 12 to exit therefrom at an aperture 36 in the cushion 20. With reference now to FIG. 5, a schematic diagram of a system 40 for monitoring cervical and/or vaginal capillary blood flow using the devices of FIGS. 1 and 1A, is illustrated schematically. With reference first to the sensor 14', which is representative of each of sensors 14a–f, the transmitters 24 include respective light emitting diodes (the six transmitters being shown schematically as two diodes) connected in a single series arrangement having a first terminal 42 coupled through a wire 34a to the equipment ground of a blood flow signal producing circuit 44. A wire 34b couples the opposite end of the series connected diodes to a second terminal 46 to receive an illuminating voltage. The illuminating voltage is provided as a pulse train, such that the transmitters 24 produce pulses of infrared radiation 48 directed into the adjacent tissue. Reflected portions 50 of the pulses 48 are incident on the photoresponsive element 26, provided in the form of a phototransistor, thus to render the collector-to-emitter circuit thereof conductive in proportion to the incident radiation 50. The emitter of transistor 26 is connected to equipment ground at first terminal 42 and its collector is connected to a respective one of three input terminals of the circuit 44 through a wire 34c. Each of the three input terminals of the circuit 44 is AC coupled through a respective capacitor 52 to a respective input terminal of an adding circuit 54. Adding circuit 54 provides an output signal at an output terminal 56 thereof, the output signal being proportional to the sum of the input signals received by the adding circuit 54, and therefore, representative of their average value. This signal provided on terminal 56 may then be displayed, for example, on the screen of an non-fade oscilloscope or recorded by means of a strip chart recorder for clinical analysis, or stored in memory for future clinical analysis.

Two systems of the type illustrated schematically in FIG. 5 may be provided, a first system for providing a signal representative of capillary blood flow in the cervix which receives input signals from sensors 14a–14c, and a second system for producing a signal representative of capillary blood flow in the vaginal wall and therefore, receiving input signals from the sensors 14d–f. Accordingly, two signals will be produced, one representative of capillary blood flow in the cervix and the other representing capillary blood flow in the vagina. These signals may be displayed and/or processed so they may be compared by the clinician to obtain valuable diagnostic information. In accordance with one method of comparison, the two signals are displayed with respect to a common time base. In accordance with a further method of comparing these signals, a third signal representative of differences between the first and second signals is produced to provide the clinician with a separate signal representing a comparison of the first two signals. This third signal is produced in accordance with one advantageous method by subtracting one of the first and second signals from the other. In this manner, these signals provide a measure of the similarities and differences between capillary blood flow patterns in the cervix and in the vagina, in order to aid in the diagnosis of conditions specific to the uterus as well as those affecting pelvic circulation in general. In the antepartum, therefore, this method is useful for diagnosing conditions such as premature labor and utero-placental insufficiency, indicated by reduced circulation in the uterus as compared to pelvic circulation in general. In the non-pregnant female, enhanced capillary blood flow in the cervix compared with capillary blood flow in the vagina serves potentially to indicate the time of ovulation when compared to the difference between cervical capillary blood flow and vaginal capillary blood flow at other times during the menstrual circle.

A further application of the present invention is to provide a comparison of capillary blood flow in the cervix and vagina with capillary blood flow in the woman's forehead at the anastomosis of the supratrochlear branches of the ophthalmic artery, the latter representing the woman's general circulatory well being. The capillary blood flow in the woman's forehead may be obtained by pressing a sensor of the type shown in FIGS. 3 and 4 against the forehead and maintaining the sensor so positioned with the use of a head strap. The capillary blood flow signal is produced using a system such as that illustrated in FIG. 5. A comparison of the first and second signals is produced by any of the methods described above for comparing the cervical capillary blood flow signal with the vaginal capillary blood flow signal. This method is particularly useful for comparing pelvic blood flow patterns with a blood flow pattern indicative of the woman's overall circulatory well being, and is, therefore, useful for detecting the pooling of blood in the pelvis due to the effects of conduction anesthesia, which may contribute to maternal hypotension. By comparing cervical capillary blood flow with a blood flow indicative of the woman's overall circulatory condition, the occurence of contractions indicative of premature labor are indicated. Other conditions specific to the uterus, such as ovulation, and in the case of a pregnant woman, utero-placental insufficiency may also be indicated.

The terms and expressions which have been employed are used as terms of description and is not of limitation, and there is intention in the use of such terms and expresions of excluding any equivalents of the features shown and described, or any portion thereof, it being recognized that various modifications are possible within the scope of the invention claimed.

I claim:

1. A device for disposal in fluids for use in monitoring cervical and vaginal capillary bloods flowing within vaginal and cervical walls of a woman comprising:
   sensing means for sensing said capillary bloods; and
   support means for positioning said sensing means against the vaginal and cervical walls of a woman in response to the support means being placed in the presence of said fluids.

2. The device of claim 1, wherein said support means comprise expansion means operable for pressing said sensing means against at least one of the vaginal and cervical walls.

3. The device of claim 2, wherein said support means further comprises a bladder.

4. The device of claim 2, wherein said expansion means comprise sponge means for absorbing vaginal fluids and for expanding in response to such absorption.

5. The device of claim 4, wherein said sponge means is a sponge.

6. The device of claim 1, wherein said support means is substantially toroidally shaped.

7. The device of claim 6, wherein said substantially toroidally shaped support means extends through at least about two thirds of a circle.

8. The device of claim 7, wherein said support means has an inner, concave surface and an outer, convex surface; and wherein the sensing means comprises first, second and third sensors disposed at approximately equal distances from each other about one of the inner and outer surfaces.

9. The device of claim 8, wherein said sensing means further comprise fourth, fifth and sixth sensors disposed at approximately equal distances from each other about the other of said inner and outer surfaces.

10. The device of claim 6, wherein said support means has an inner, concave surface and an outer, convex surface; and said sensing means comprise a plurality of sensors positioned about at least one of the inner and outer surfaces.

11. The device of claim 10, wherein the plurality of sensors are further positioned about both the inner and outer surfaces.

12. The device of claim 1, wherein upon positioning said sensing means near said vaginal and cervical walls said support means conforms to the shape of a womans cervix.

13. The device of claim 1, wherein said support means comprises a form-sustaining spine and a cushion positionable for contacting the cervical and vaginal walls.

14. The device of claim 13, wherein upon positioning said sensing means near said vaginal and cervical walls said spine conforms to the shape of a woman's cervix.

15. The device of claim 13, wherein the cushion expands when placed near the cervical wall and the vaginal wall.

16. The device of claim 13, wherein the cushion when placed near the cervical and vaginal walls absorbs fluids and expands in response to such absorption.

17. The device of claim 16, wherein the cushion is a sponge.

18. The device of claim 1, wherein the sensing means comprises a plurality of sensors each of which includes a base having a surface positioned to face one of the cervical and vaginal walls, infrared transmitting means for transmitting infrared radiation into said one of the cervical and vaginal walls, said transmitting means supported by the base and having a portion which protrudes through said surface and which is adapted to be pressed against said one of the cervical and vaginal walls, and means for detecting infrared radiation received from said one of the cervical and vaginal walls supported by the base and having a portion which protrudes through the surface thereof to be pressed against said one of the cervical and vaginal walls.

19. The device of claim 18, wherein the transmitting means comprises a plurality of light emitting diodes coupled in series.

20. A method of evaluating a physiological condition of a woman comprising the steps of:
   producing a first signal representing one of the cervical and vaginal capillary blood flows in the woman; and
   producing a second signal representative of capillary blood flow in a woman's forehead at the anastomosis of the supratrochlear branches of the ophthalmic artery; and
   comparing the first and second signals.

21. The method of claim 20, wherein the step of comparing the first and second signals comprises displaying the first and second signals with respect to a common time base.

22. The method of claim 20, wherein the step of comparing the first and second signals comprises producing a third signal representative of differences between the first and second signals.

23. The method of claim 22, wherein the step of producing the third signal comprises subtracting one of the first and second signals from the other.

24. The method of claim 20, wherein the physiological condition is premature labor.

25. The method of claim 20, wherein the physiological condition is ovulation.

26. The method of claim 20, wherein the physiological condition is uteroplacental insufficiency.

27. The method of claim 20, wherein the physiological condition is maternal hypotension.

* * * * *